United States Patent
Nakao et al.

(10) Patent No.: US 6,589,740 B2
(45) Date of Patent: Jul. 8, 2003

(54) METHOD AND DEVICE FOR DETECTING HYBRIDIZATION REACTION

(75) Inventors: Motonao Nakao, Kanagawa (JP); Kenji Yamamoto, Kanagawa (JP); Junji Yoshii, Kanagawa (JP); Katsuya Mizuno, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 09/802,804

(22) Filed: Mar. 9, 2001

(65) Prior Publication Data

US 2002/0022226 A1 Feb. 21, 2002

(30) Foreign Application Priority Data

Mar. 10, 2000 (JP) .......................... 2000-067684

(51) Int. Cl.[7] .......................... C12Q 1/68; C07H 21/02; C07H 21/04
(52) U.S. Cl. .......................... 435/6; 536/23.1; 536/24.3
(58) Field of Search .......................... 435/6; 536/23.1, 536/24.3

(56) References Cited

PUBLICATIONS

Thiel, A. J. et al., "In Situ Surface Plasmon Resonance Imaging Detection of DNA Hybridization to Oligonucleotide Arrays on Gold Surfaces", Anal. Chem., vol. 69, pp. 4948–4956 (1997).*

* cited by examiner

Primary Examiner—Kenneth R. Horlick
Assistant Examiner—Teresa Strzelecka

(57) ABSTRACT

The present invention detects and quantities only specific hybridization bindings. A biochip 10 which is spotted with a plurality of probe biopolymers is accommodated in a container 20 into which a washing solution is supplied from a liquid supplying unit 23. A heat block 31 controls the temperature of the biochip according to a predetermined time pattern. A pickup unit 55 picks up an image of the spot surface of the biochip at predetermined pickup intervals. The plurality of images picked up with the pickup unit are stored in a computer 40. By analyzing the images for individual spots, hybridization can be detected with high reliability for every spots without being influenced by optimal hybridization temperatures which differ depending upon the types of probes on the spots.

3 Claims, 12 Drawing Sheets

| Spot ID (91) | Estimated dissociation temperature (°C) (92) | Effective intensity (%) (93) | Judgment (94) |
|---|---|---|---|
| 1 | 72 | 80 | ◎ |
| 2 | 80 | 50 | △ |
| 3 | 85 | 80 | ◎ |
| 4 | 80 | 72 | ○ |
| 5 | 78 | 30 | × |
| 6 | 80 | 50 | △ |
| ⋮ | ⋮ | ⋮ | ⋮ |

METHOD AND DEVICE FOR DETECTING HYBRIDIZATION REACTION

This application claims priority to Japanese Application Serial No. 67684/2000, filed Mar. 10, 2000.

FIELD OF THE INVENTION

The present invention relates to a method and a device for detecting a hybridization reaction between probe biopolymers such as probe DNAs spotted on a biochip and a sample biopolymer such as fluorescence-labeled or chemiluminescence-labeled DNA.

BACKGROUND OF THE INVENTION

In the fields of molecular biology and biochemistry, biopolymers such as nucleic acids and proteins from organisms are identified and/or fractionated in order to search for useful genes or to diagnose diseases. A hybridization reaction is frequently used as a pretreatment for such process, where a target molecule in a sample is hybridized to nucleic acids or proteins having known sequences. In order to process mass samples in a short time, a biochip is used whose surface is provided with a plurality of features arranged in a matrix. For example, different DNA probes are spotted and immobilized on the respective features of the biochip. Such biochip is placed into a reaction container together with sample DNA to allow the fluorescence-labeled sample DNA to hybridize with the probes immobilized on the respective features of the biochip. Thereafter, the biochip is irradiated with excitation light to measure fluorescent intensity of each feature. Based on the measured fluorescent intensities, the binding levels between the respective probes and the sample DNA are obtained and converted into desired information.

FIGS. 13A and 13B are schematic views illustrating a conventional hybridization reaction using a biochip. As shown in FIG. 13A, a sample DNA solution 114 is applied onto a DNA spot region 112 of a biochip 110 provided with a plurality of DNA spots. Then, the biochip 110 is covered with a glass cover 116. As shown in FIG. 13B, the biochip 110 is then enclosed in a sealed container 120 to be subjected to hybridization in a chamber provided with a temperature controller. The temperature inside the chamber is maintained at a predetermined temperature. Although an optimal temperature for hybridization generally varies according to each DNA spot, the temperature is set to an average optimal temperature to perform hybridization to all of the spots. Thereafter, the biochip is washed to remove the non-hybridized sample DNA, followed by reading a fluorescence from fluorescent substance labeling the sample DNA with a fluorescence reader.

Conventionally, hybridization is performed while setting the temperature to an average dissociation temperature regardless of difference among individual optimal temperatures of the respective spots on the biochip. Therefore, at a spot having an optimal temperature lower than the set average temperature, binding between the complementary DNAs cannot be maintained, lowering the hybridization efficiency and resulting in a lower detected signal intensity as compared to an intrinsic signal intensity. On the other hand, at a spot having an optimal temperature higher than the set average temperature, non-specific binding is caused between non-complementary DNAs, resulting in a higher detected signal intensity as compared to an intrinsic signal intensity. According to a hybridization detection using such a conventional biochip, hybridization is performed at a constant temperature regardless of the difference among the optical temperatures of the respective spots, and the results read with the fluorescence reader are used to compare DNA levels. Thus, the quantitation results have been questionable.

In view of such conventional problems, the present invention has objectives of providing a method and a device for detecting hybridization, which are capable of detecting and quantifying only specific bindings resulting from the hybridization.

SUMMARY OF THE INVENTION

In order to realize the above-mentioned objectives, the present invention is provided with a controller having a program capable of altering a temperature of the biochip at different time points, an excitation light source and a cooled CCD camera used for detection. A sample biopolymer is hybridized to probe biopolymers on the spots of the biochip at a low temperature. The temperature is gradually raised while supplying a washing solution. Images of an entire surface of the biochip at predetermined temperatures are taken to detect fluorescence from each spot. By performing hybridization while altering from lower temperature to higher temperature, the status of the hybridization can be confirmed. As a result, hybridizations at every single spots can be detected with high reliability without being influenced by optimal hybridization temperatures which differ by types of probe biopolymers at respective spots.

A method for detecting a hybridization reaction according to the present invention comprises the steps of: binding a sample biopolymer to a biochip having a reaction region on which a plurality of probe biopolymers are separately spotted; and detecting hybridization reactions at individual spots by raising the temperature of the biochip.

In the step of detecting the hybridization reaction, a washing solution is preferably run to the reaction region of the biochip. By running the washing solution, a sample biopolymer non-hybridized to or dissociated from the probe biopolymers can be removed from the spots, thereby reducing occurrence of noise upon detection.

Furthermore, a method for detecting a hybridization of the invention comprises the steps of: placing, in a container, a biochip having a reaction region on which a plurality of probe biopolymers are separately spotted; injecting a sample biopolymer into the container; maintaining the biochip in the container at a constant temperature; and taking images of the reaction region of the biochip at predetermined timings while running a washing solution into the container and while changing the temperature of the biochip according to a predetermined time pattern. In the step of maintaining the biochip in the container at a constant temperature, a sample biopolymer is injected to be hybridized to the probe biopolymers on the spots. While supplying the washing solution into the container, the temperature of the biochip is preferably altered according to a simple temperature-raising time pattern.

Preferably, the sample biopolymer is fluorescence-labeled, and fluorescent intensities of individual spots are analyzed based on the images. Degrees of the hybridization reactions between the sample biopolymer and the individual target biopolymers immobilized on the spots may be detected based on changes of a fluorescent intensity of each spot with time. Information of a temperature upon a rapid fall of the fluorescent intensity is acquired, so as to compare it with a dissociation temperature estimated from the molecular structure of the probe biopolymer, thereby improving reliability of detection of a hybridization reaction. When the temperature upon a rapid fall is generally equal to the estimated dissociation temperature of the probe biopolymer immobilized on the spot, it may be judged that specific hybridization took place. On the other hand, when the two temperatures are obviously different from each other, it may be judged that the sample biopolymer is bound non-specifically.

A device for detecting a hybridization reaction according to the present invention comprises: a container for accommodating a biochip having a reaction region on which a plurality of probe biopolymers are separately spotted; a temperature controller for controlling the temperature of the biochip placed in the container according to a predetermined time pattern; a unit for supplying a washing solution into the container; an image pickup unit for taking an image of the reaction region of the biochip in the container; a controller for controlling timing for taking the image with the image pickup unit; and a storage unit for storing a plurality of images taken with the image pickup unit. The temperature controller preferably controls the temperature of the biochip according to a simple temperature-raising time pattern. Preferably, the device comprises a function of displaying changes of a fluorescent intensity of a selected spot with time.

BRIEF DESCRIPTION OF THE DRAWINGS

FIG. 9 is a diagram showing a numerically-expressed image, containing a background value.

FIG. 10 is a diagram showing a numerically-expressed image, removed of the background value.

FIG. 12 is a table illustrating a method for confirming the reliability for a single spot on the biochip.

DETAILED DESCRIPTION OF THE INVENTION

Hereinafter, embodiments of the present invention will be described with reference to the attached drawings. Herein, DNA is used as both probe biopolymers (hereinafter, simply referred to as "probes") and a sample biopolymer. However, application of the present invention is not limited to such combination. The present invention is equivalently applicable when the biopolymers are RNAs, amino acids (proteins), sugar chains or complexes thereof (glycoprotein etc.).

Figure 1:
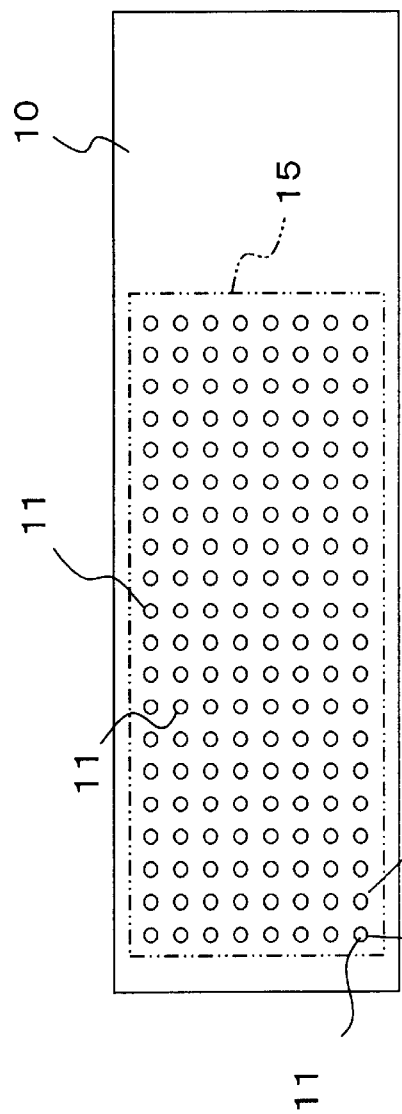
FIGS. 1A and 1B are schematic views showing a biochip used in the present invention.
Figure 1:
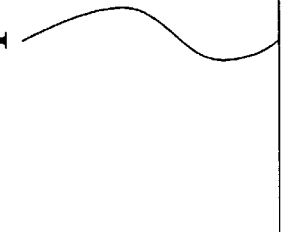

FIGS. 1A and 1B are schematic views showing an exemplary biochip used in the present invention. As shown in FIG. 1A, a biochip 10 is provided with a plurality of probes such as DNAs spotted and immobilized on a reaction region 15 defined on a substrate such as a glass slide. Respective spots 11 on the biochip 10 consist of different probes which are individually subjected to specific hybridization to a variety of target DNAs.

As shown in FIG. 1B, DNA consists of nucleic acids containing four types of bases, A (adenine), T (thymine), C (cytosine) and G (guanine). A (adenine) binds to T (thymine) and C (cytosine) binds to G (guanine) via hydrogen bondings. Two hydrogen bondings are formed between A and T whereas three hydrogen bondings are formed between C and G. No hydrogen bonding is formed for pairs other than these combinations. Hybridization causes DNA to chemically bind to a complementary DNA via hydrogen bonding. A bonding energy upon this hybridization can be estimated from constitutive bases of the DNA. Accordingly, a dissociation temperature Tm between specifically-binding DNAs under a hybridization reaction can also be estimated by the following [equation 1]. Since the numbers of hydrogen bondings between A and T, and C and G are two and three, respectively, a higher CG content generally results in a higher bonding energy. This is taken into consideration in [Equation 1].

$$Tm(° C.)=81.5+16.6\times\log[S]+0.41\times(\% \ GC)-(500/n) \quad \text{[Equation 1]}$$

where [S] is a mol number of salts, (% GC) is a GC content in an oligonucleotide, and n is a length (pb) of the oligonucleotide. [Equation 1] is merely an estimation and generally there may be an error, for example, as a result of an influence from adjacent molecules (herein, DNA) and the like, or a hydrogen bonding between complementary strand moieties inside a single DNA (self complementary strand).

Figure 2:
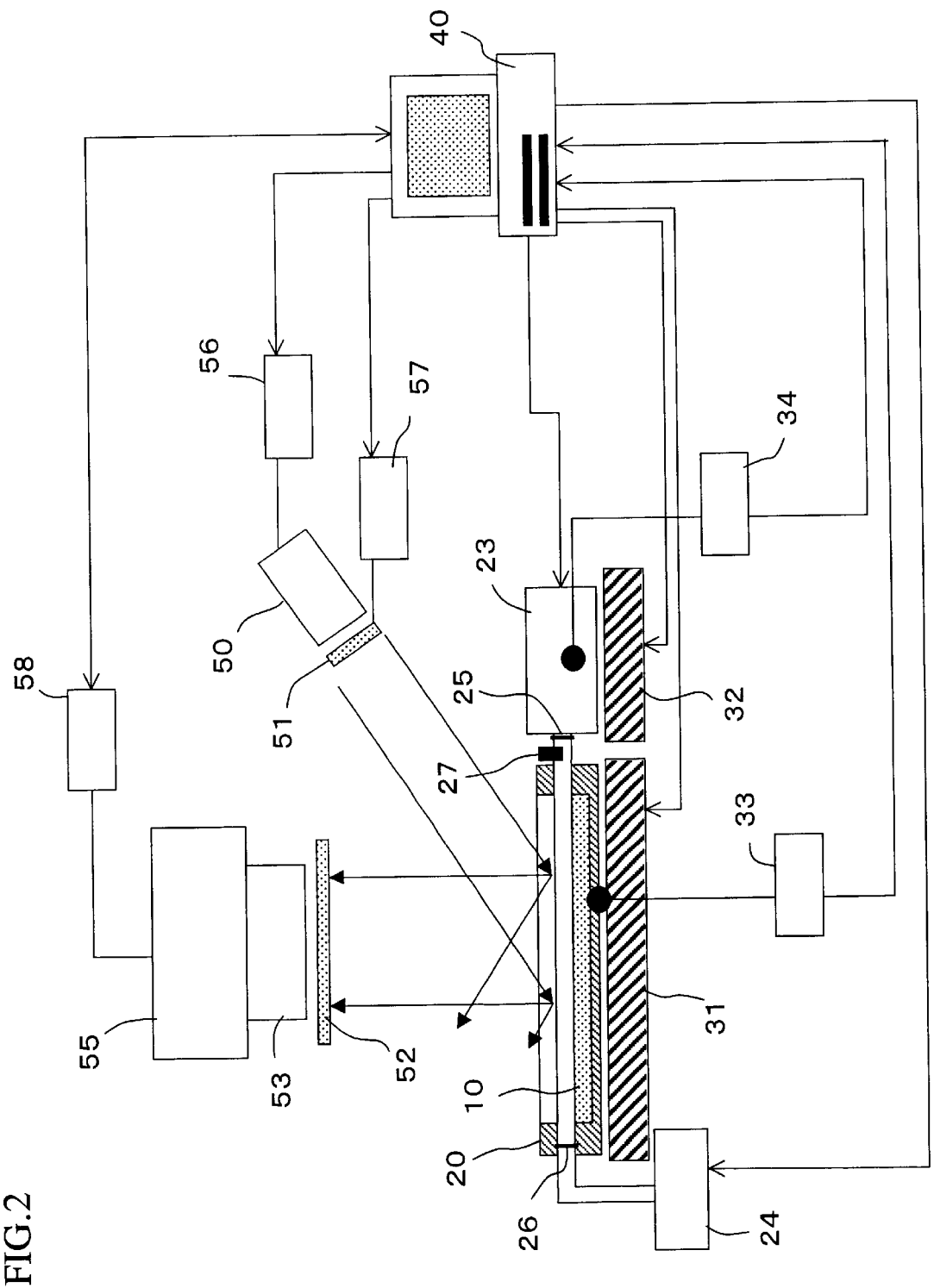
FIG. 2 is a schematic view of an exemplary chip hybridization reaction detector of the invention.

FIG. 2 is a schematic view showing an outline of an exemplary device of the invention for detecting a hybridization reaction of a chip. This device for detecting a hybridization reaction is provided with a hybridization reactor and a fluorescence detector. The hybridization reactor is provided with a pressurized-type supplying unit 23 for supplying a washing solution to the biochip 10 inside a chip case 20, a heat block 31 for heating the biochip 10 inside the chip case 20, a heat block 32 for heating a solution inside the pressurized-type supplying unit 23, a thermometer 33 for measuring a temperature of the biochip 10, a thermometer 34 for measuring a temperature of the solution inside the pressurized-type supplying unit 23, etc. The outputs from the thermometers 33 and 34 are input into a computer 40, which in turn controls the heat blocks 31 and 32. The fluorescence detector is provided with an excitation light source 50, an optical filter 51 for excitation light, an optical filter 52 for received light, an optical system 53 for the received light, an image pickup unit (cooled CCD camera) 55, etc. The excitation light source 50, the optical filters 51 and 52, and the image pickup unit 55 are controlled by the computer 40 via controllers 56, 57 and 58, respectively. In addition to control of the units, the computer 40 performs operations such as a processing of an image taken with the image pickup unit 55, data analysis, displaying results of the analysis, etc., by following the internal data analyzing programs.

Figure 3:
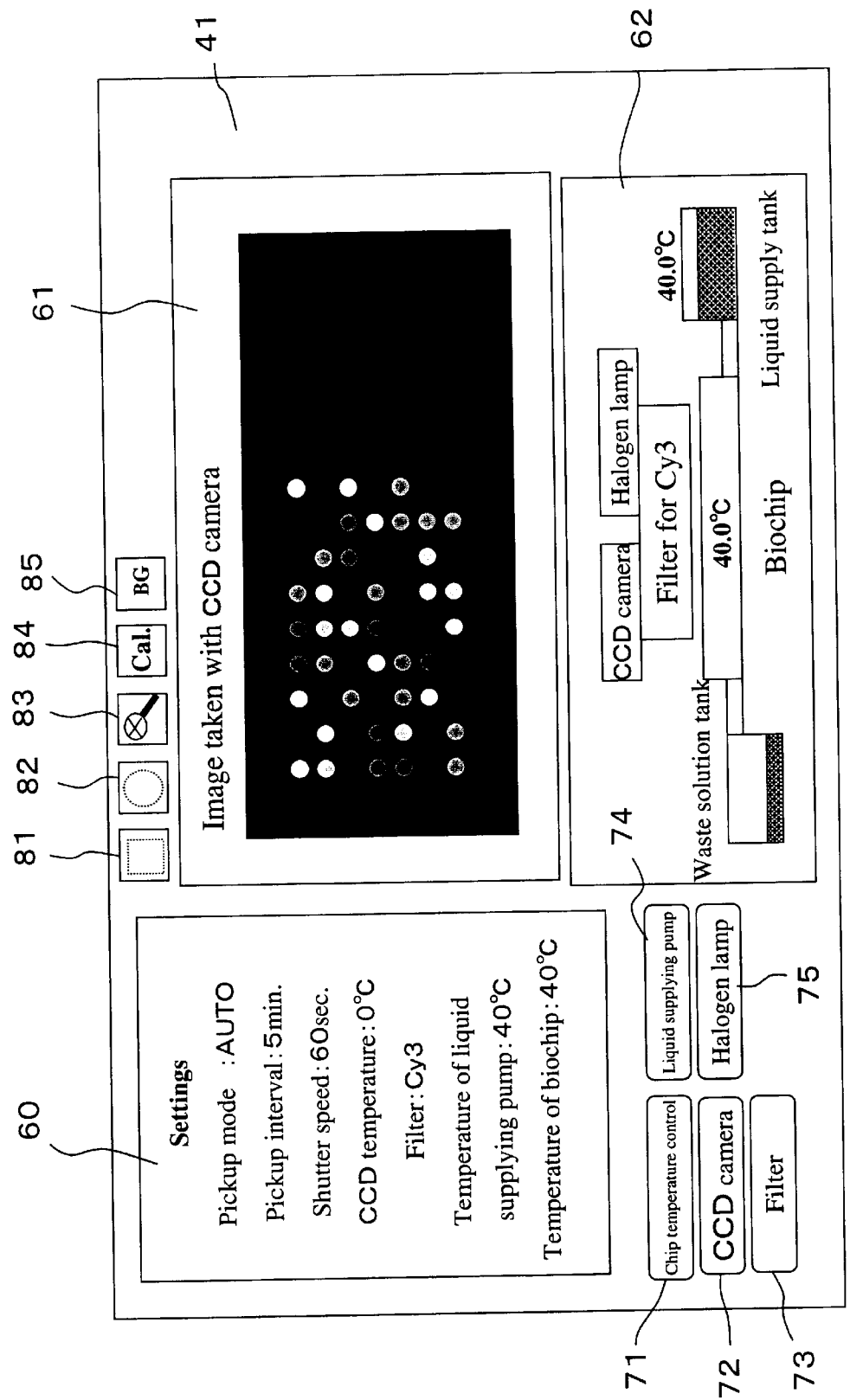
FIG. 3 is a schematic view illustrating a monitor screen.

FIG. 3 is a schematic view showing an exemplary screen displayed on the computer. On the display screen 41, a settings displaying section 60, a readout image displaying section 61, an operation status displaying section 62, buttons 71 to 75 for operations, and various tool buttons 81 to 85 are displayed. On the settings displaying section 60, settings for image pickup are displayed. On the readout image displaying section 61, the latest picked up fluorescence image of the biochip 10 is displayed. On the operation status displaying section 62, present status of the device is displayed. The display window in the display screen 41 can be switched, for example, to display a graph shown in FIG. 11 or a table shown in FIG. 12.

The chip temperature control button 71 is provided for setting a temperature of the biochip 10. As the button 71 is clicked, a chip temperature controlling window (not shown) appears on which a pattern of the temperature changes of the biochip 10 with time is set. The computer 40 compares the present temperatures read with the thermometers 33 and 34 to the set temperatures to control the temperatures by using the Peltier heat blocks 31 and 32. The CCD camera button 72 is provided to control the cooled CCD camera 55. As the button 72 is clicked, a camera setting window (not shown) appears on which a cooling temperature, pickup intervals, and a shutter speed of the cooled CCD camera 55 and the like can be set. As the filter button 73 is clicked, a filter setting window (not shown) appears on which the excitation light optical filter 51 and the received light optical filter 52 can be selected according to the type of the fluorescence label. According to the settings made by clicking the filter button 73, the filter switching unit 57 simultaneously selects and switches the excitation light optical filter 51 and the received light optical filter 52 to suit the fluorescent substance of interest. As the liquid supplying pump button 74 is clicked, a setting window (not shown) appears on which a temperature and a flow rate of the washing solution in the pressurized-type supplying unit 23 as well as ON/OFF of liquid supply can be set. When the halogen lamp button 75 is clicked, a lamp condition setting window appears on which a source voltage of the halogen lamp 50 (the excitation light source) can be set. According to this setting, the halogen lamp controller 56 controls the halogen lamp 50 to adjust the intensity of the excitation light.

Figure 4:
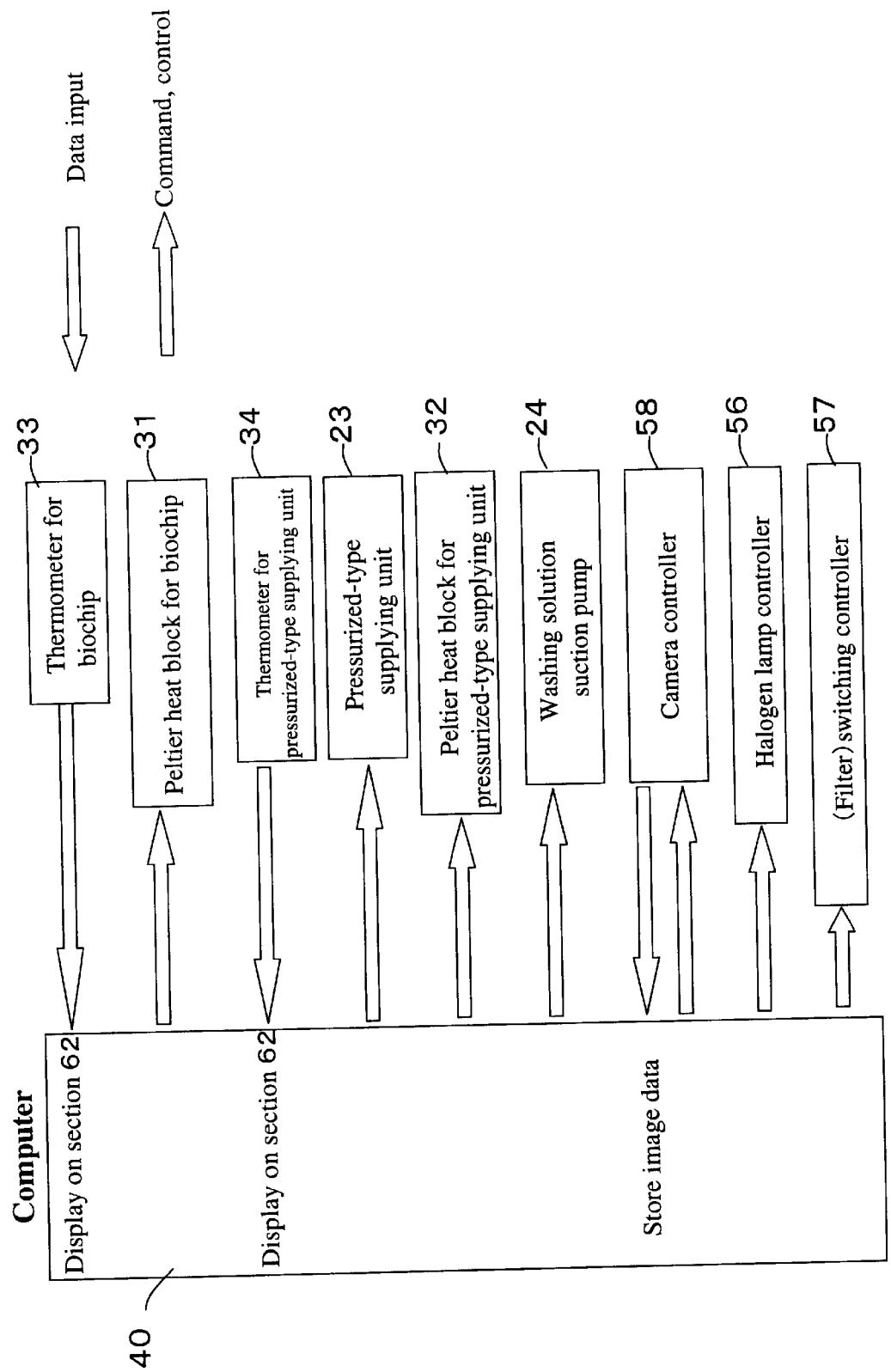
FIG. 4 is a schematic diagram showing relationships of flows of data to the computer and control on respective units by the computer.

FIG. 4 is a schematic diagram showing flows of data input into the computer and the control made by the computer on the respective units of the device. In the figure, the arrows directing toward the computer 40 represent data input into the computer 40 while the arrows directing out from the computer 40 represent commands and control made by the computer 40 on the respective units of the device. In accordance with the set conditions displayed on the settings displaying section 60, the computer 40 controls temperatures of the heat blocks 31 and 32 and a temperature of the cooled CCD camera 55, and controls the halogen lamp controller 56 and the filter switching controller 57. The computer 40 also controls the pumpings of the pressurized-type supplying unit 23 and the suction-type discharging unit 24. The data of temperatures of the biochip 10 and the pressurized-type supplying unit 23 is input into the computer 40 via the thermometers 33 and 34 and displayed on the operation status displaying section 62. The computer 40 sequentially reads out fluorescence image data of the biochip 10 output from the camera controller 58 at predetermined image pickup intervals, and store it in a storage medium.

Hereinafter, operations and control for a hybridization reaction and hybridization detection using the above-described device for detecting a chip hybridization reaction will be described.

First, the prepared biochip 10 is placed into the chip case 20. A fluorescence-labeled sample DNA solution is injected into a solution injection cavity 27 which is provided at an liquid supply path between the pressurized-type supplying unit 23 and the chip case 20. The injected sample DNA solution flows into the chip case 20 with the flow of the hybridization solution (also used as a washing solution) sent from the pressurized-type supplying unit 23. Once the sample DNA solution enters the chip case 20, the pressurized-type supplying unit 23 is turned off to halt the flow of the hybridization solution, thereby allowing a long period of hybridization while maintaining the temperature of the chip case 20 and the biochip 10 to a relatively low temperature (about 370 C.) by controlling the heat block 31.

Thereafter, to confirm the hybridization status of the biochip 10 with the fluorescence detector, the washing solution is sent from the pressurized-type supplying unit 23 into the chip case 20 accommodating the biochip 10 at a predetermined flow rate to discharge sample DNA that did not hybridize with the probe DNAs on the biochip 10 together with the washing solution by using the suction-type discharging unit 24. The washing solution used may be the same as the hybridization solution. Back-flow valves 25 and 26 are provided at the inflow port and the outflow port of the chip case 20 to prevent backflow of the washing solution. Then, the entire surface of the biochip 10 is irradiated with excitation light from the excitation light source 50. According to the present example, the excitation light source 50 is a halogen lamp which, by the use of the excitation light optical filter 51, radiates only light at a wavelength appropriate for exciting the fluorescence substance labeling the sample DNAs. When chemiluminescence or the like is utilized for detection, excitation light is not necessary and thus the excitation light source 50 is turned off.

Figure 5:
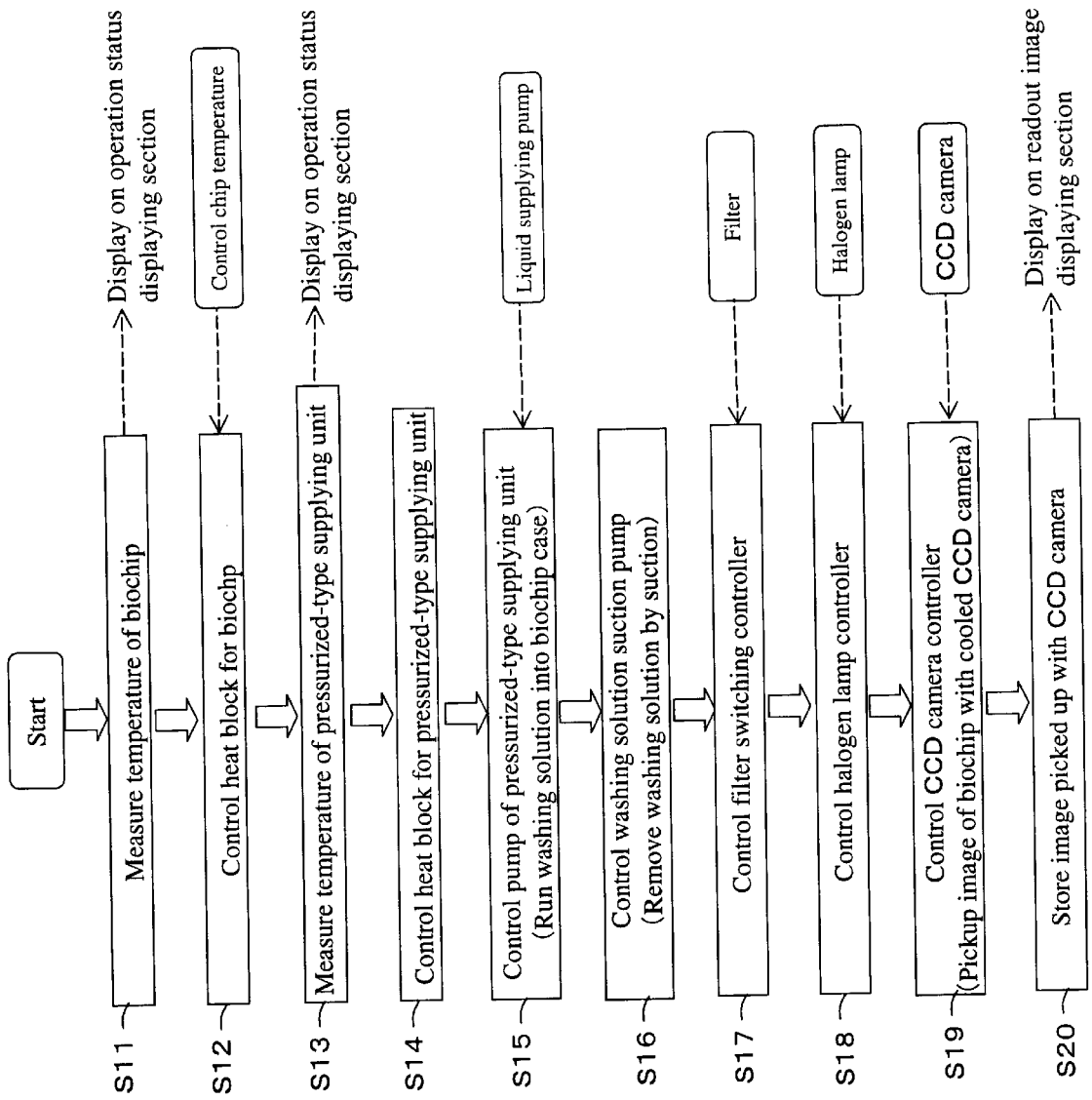
FIG. 5 is a flowchart illustrating a flow of processes for confirming a hybridization status.

FIG. 5 is a flowchart showing processes executed by the program controlling the hardware of the device for detecting the chip hybridization reaction upon confirming the hybridization status with the fluorescence detector. The displaying sections and the setting buttons on the display screen 41 (see FIG. 3) corresponding to the control are shown on the right of the flowchart.

First, the temperature of the biochip 10 is measured with the thermometer 33 (S11). The measurement result is displayed on the operation status displaying section 62. Then, by comparing the measured temperature with the temperature set at each predetermined time point, the chip temperature control button 71 controls the heat block 31 to adjust the measured temperature to be equal to the set temperature at that time point (812). The temperature of the pressurized-type supplying unit 23 is measured with the thermometer 34 and displayed on the operation status displaying section 62 (S13). Similarly, the heat block 32 is controlled to adjust the temperature of the pressurized-type supplying unit 23 to be equal to the set temperature (S14). Then, the pump of the pressurized-type supplying unit 23 is controlled to supply the washing solution into the biochip case 20 according to a flow rate set with the liquid supply pump button 74 (S15). At the same time, the suction-type discharging unit 24 is controlled to remove an excess of the washing solution by suction (S16).

In order to adapt to the excitation light wavelength and the fluorescence wavelength of the fluorescent substance to be detected, the filter switching controller 57 is controlled to set the excitation light optical filter 51 and the received light optical filter 52 by following the settings made with the filter button 73 (S17). Then, the halogen lamp controller 56 is controlled according to the setting made with the halogen lamp button 75 to determine a light source intensity (S18). Next, the CCD camera controller 58 is controlled according to the settings set with the CCD camera button 72 to pick up an image of the biochip 10 with the cooled CCD camera 55 under the set conditions (S19). The picked up image is stored in the storage medium of the computer 40 and displayed on the readout image displaying section 61 on the display unit (S20). The measurement control is performed as described above, and eventually, image files of the biochip 10 picked up with the cooled CCD camera 55 are sequentially stored in the storage medium of the computer 40.

In general, hybridization at a low temperature will result in hybridization between probe DNA with sample DNA with low complementation. According to the present invention, hybridization is detected while the temperature of the biochip 10 and its surrounding temperature are gradually raised according to a predetermined time pattern. The time pattern of the temperature changes of the biochip 10 is predetermined in the computer 40 with the chip temperature control button 71. The computer 40 compares the present temperature measured with the thermometer 33 with the set temperature and controls the Peltier heat block 31 for adjustment so that the temperature changes of the biochip 10 follows the predetermined time pattern. The computer 40 also measures the temperature of the solution supplied from the pressurized-type supplying unit 23 with the thermometer 34 and controls the Peltier heat block 32 such that the temperature of the solution becomes the same as that of the biochip 10 in the chip case 20. Thus, the pressurized-type supplying unit 23 supplies the solution at a temperature equal to that of the biochip 10 into the chip case 20. While the solution is supplied from the pressurized-type supplying unit 23, a waste solution is discharged by suction from the chip case 20 with the suction-type discharging unit 24.

As the temperatures of the washing solution and the biochip 10 are gradually raised, sample DNAs with lower complementation begins to be dissociated at an earlier stage at a lower temperature. Although it can be viewed that eventually only sample DNA with high complementation (i.e., the target DNA of interest) should remain bound to the probe, this target sample DNA will also be dissociated when the temperature of the biochip 10 and its surrounding temperature exceed the dissociation temperature of the target DNA, resulting in rapid fall of fluorescent intensity of that spot. Accordingly, it is deemed that hybridization detected around the dissociation temperature (a temperature slightly lower than the dissociation temperature) is the hybridization to the target.

Herein, hybridization is performed using sample DNA labeled with fluorescent substance Cy3 (excitation wavelength 550 nm, fluorescence wavelength 570 nm). Fluorescence emitted from the fluorescent substance is selectively transmitted through the received light optical filter 52, converged with the condenser lens 53 and picked up with the highly sensitive cooled CCD camera 55. The output from the CCD camera 55 is sent to the computer 40 via the camera controller 58. In order to accommodate various types of fluorescent substances, the excitation light optical filter 51 and the received light optical filter 52 can be exchanged by the switching controller 57.

The entire image of the biochip 10 is automatically picked up with the cooled CCD camera 55 under the condition shown in the settings displaying section 60 (in the figure, at 5 minutes intervals), displayed on the image displaying section 61 and sequentially stored as image data in the storage medium of the computer 40. Information obtained from the fluorescent image of the biochip 10 is analyzed to be displayed according to changes with time and temperature, which will be described below.

Figure 6:
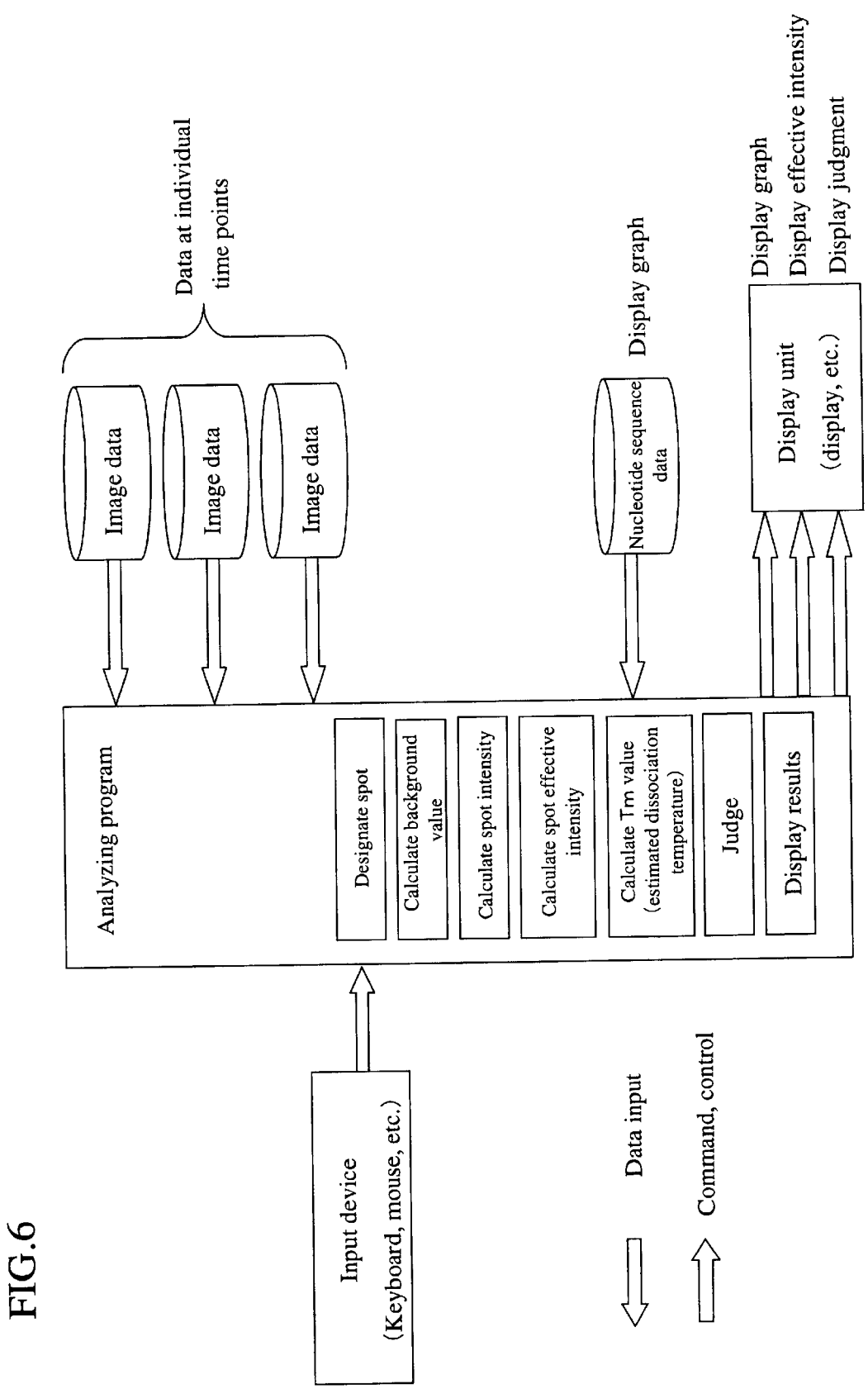
FIG. 6 is a block diagram illustrating processes executed by a data analyzing program.

FIG. 6 is a block diagram illustrating processes executed by the data analyzing program, generally showing readout of data from the computer and control by the respective sub-programs. Arrows directing left represent data read out process and arrows directing right represent commands and control.

The analyzing program includes sub-programs for designating a spot, calculating a background value, calculating a spot intensity, calculating a spot effective intensity, calculating a Tm value (estimated dissociation temperature), judging and displaying the result. The spot is designated using an input device such as a keyboard and mouse. Analysis is conducted based on image data at readout time points and nucleotide sequence data of the probe DNAs. The results of the analysis are displayed as a graph, a table or the like on the display unit.

Figure 7:
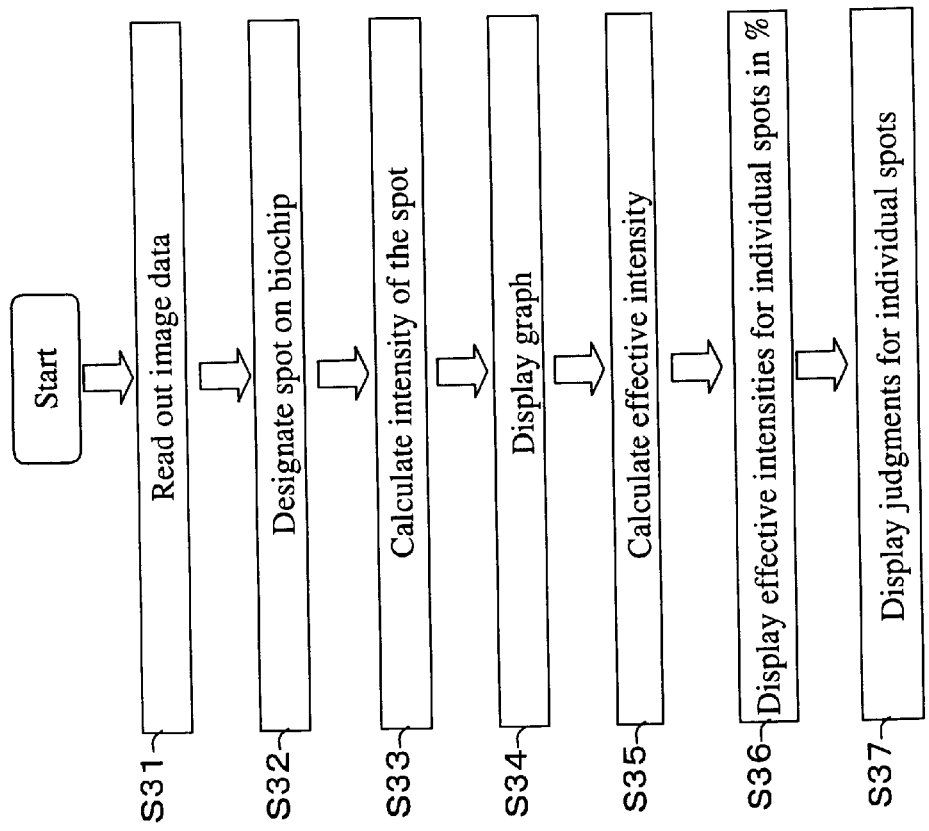
FIG. 7 is a flowchart showing an outline of processes executed by an image data analyzing program.

FIG. 7 is a flowchart showing an outline of processes executed by an image data analyzing program. The image data is stored as image files at individual image pickup time points. Analysis is conducted by reading out the image files one by one to obtain numerically-expressed fluorescent intensity of each spot on the biochip which is subtracted of the background value. Hereinafter, processes executed by the data analyzing program will be described with reference to FIGS. 8A to 8D showing the readout image displaying section 61.

Figure 8:
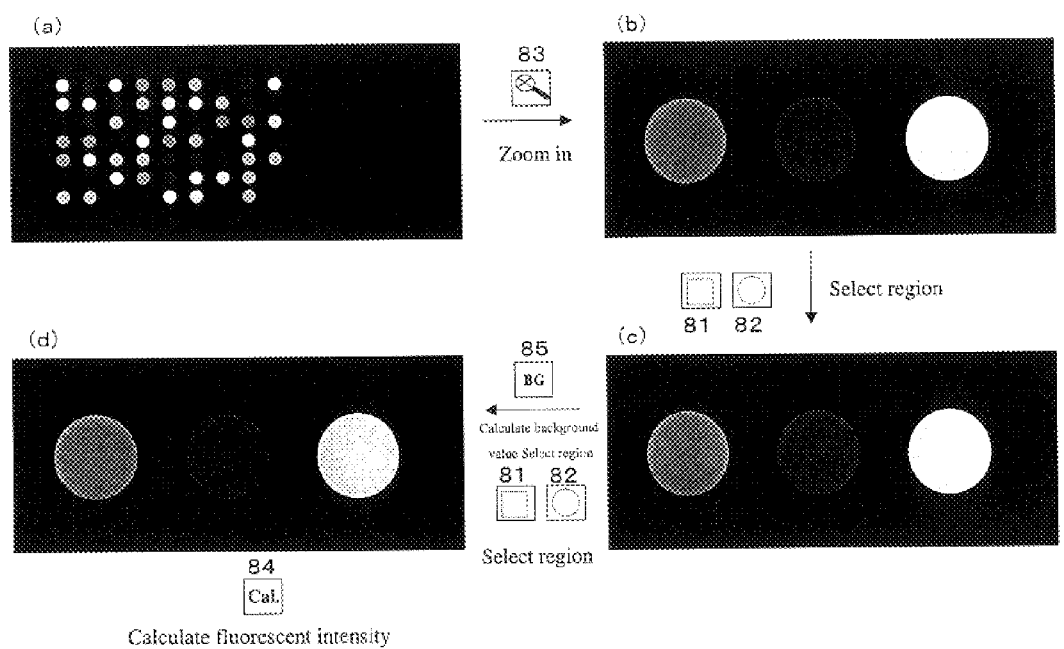
FIGS. 8A to 8D are schematic views showing readout image displays.

First, image data shown in FIG. 8A showing a hybridization status of the biochip 10 is read out (S31). A zoom-in tool 83 is used to enlarge the readout image to a suitable size as shown in FIG. 8B. Then, as shown in FIG. 8C, region selection tools 81 and 82 are used to select a background region of an appropriate size, and a background value calculation tool 85 is used to calculate a background value. The background value is always subtracted in subsequent calculations of fluorescent intensities at individual time points. After the background value calculation, the region selection tools 81 and 82 are used to select a sample region as shown in FIG. 8D (S32). An intensity calculation tool 84 is used to calculate a fluorescent intensity of the spot (S33). Based on images picked up at predetermined intervals, fluorescent intensities of the same spot at different time points are calculated. The changes of fluorescent intensities of that spot are shown as a graph with time (S34).

Figures 9, 10:
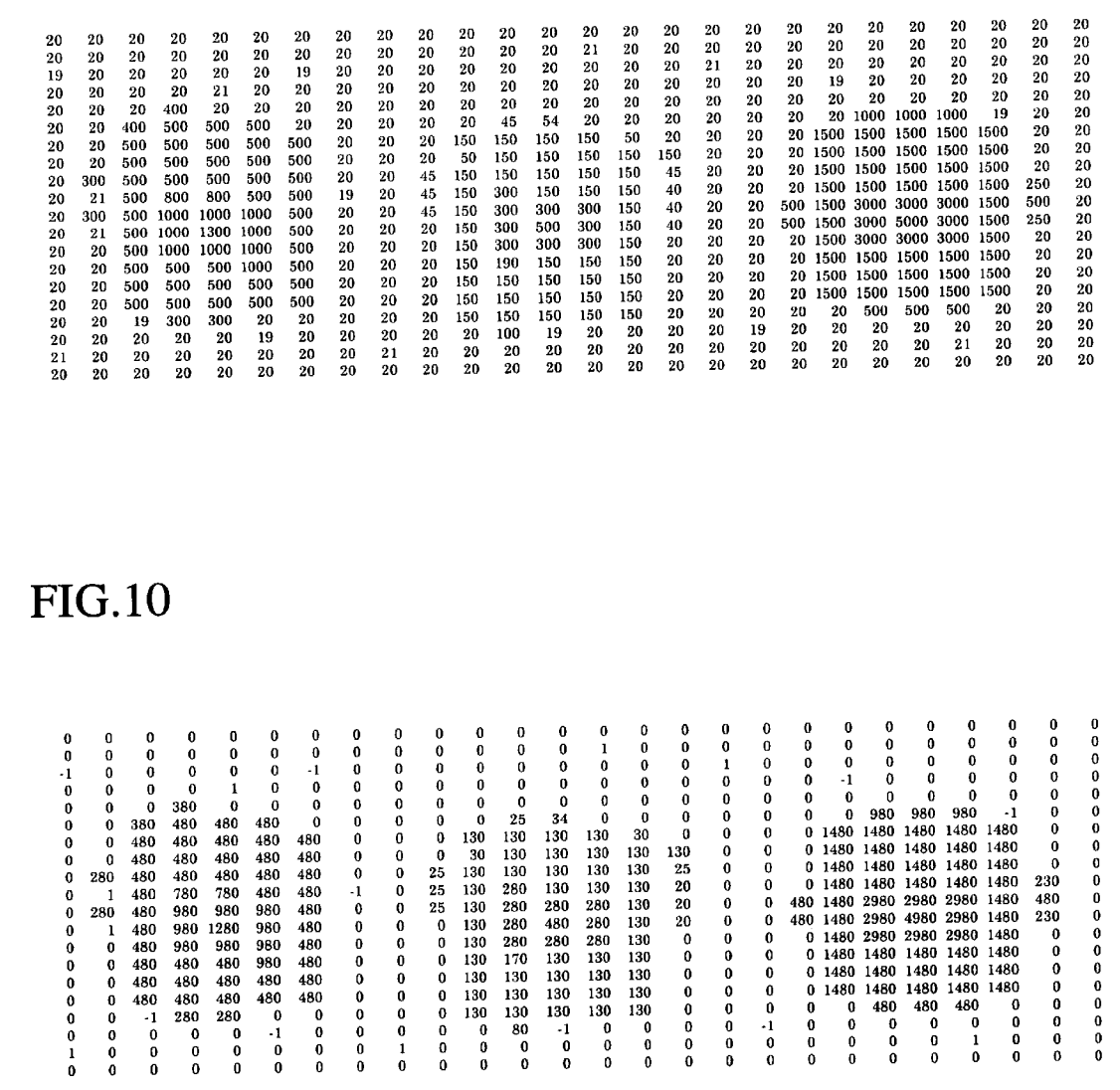

For example, the calculation in FIGS. 8A to 8D may actually be conducted as follows. In the image, the fluorescent intensity is represented by black-and-white binary but in fact the detected fluorescent intensity is represented by 16 or 8 bits per pixel. When the image enlarged with the zoom-in tool 83 is numerically expressed, it may, for example, be represented as shown in FIG. 9. When an intensity of a region in this image other than the sample spot regions (i.e., an intensity of the background region) is calculated, the average value per pixel is 20. Thus, for subsequent calculations, 20 is subtracted for every pixel. The fluorescent intensity image that underwent the background correction is shown in FIG. 10. The fluorescent intensity is calculated by summing the values in the region surrounded with the region selection tool. In the figure, the fluorescent intensities of the three spots from left are 33221, 9118 and 95777, respectively. Such image is picked up at predetermined time points (in FIG. 3, for every 5 minutes) and stored in the computer 40.

Figure 11:
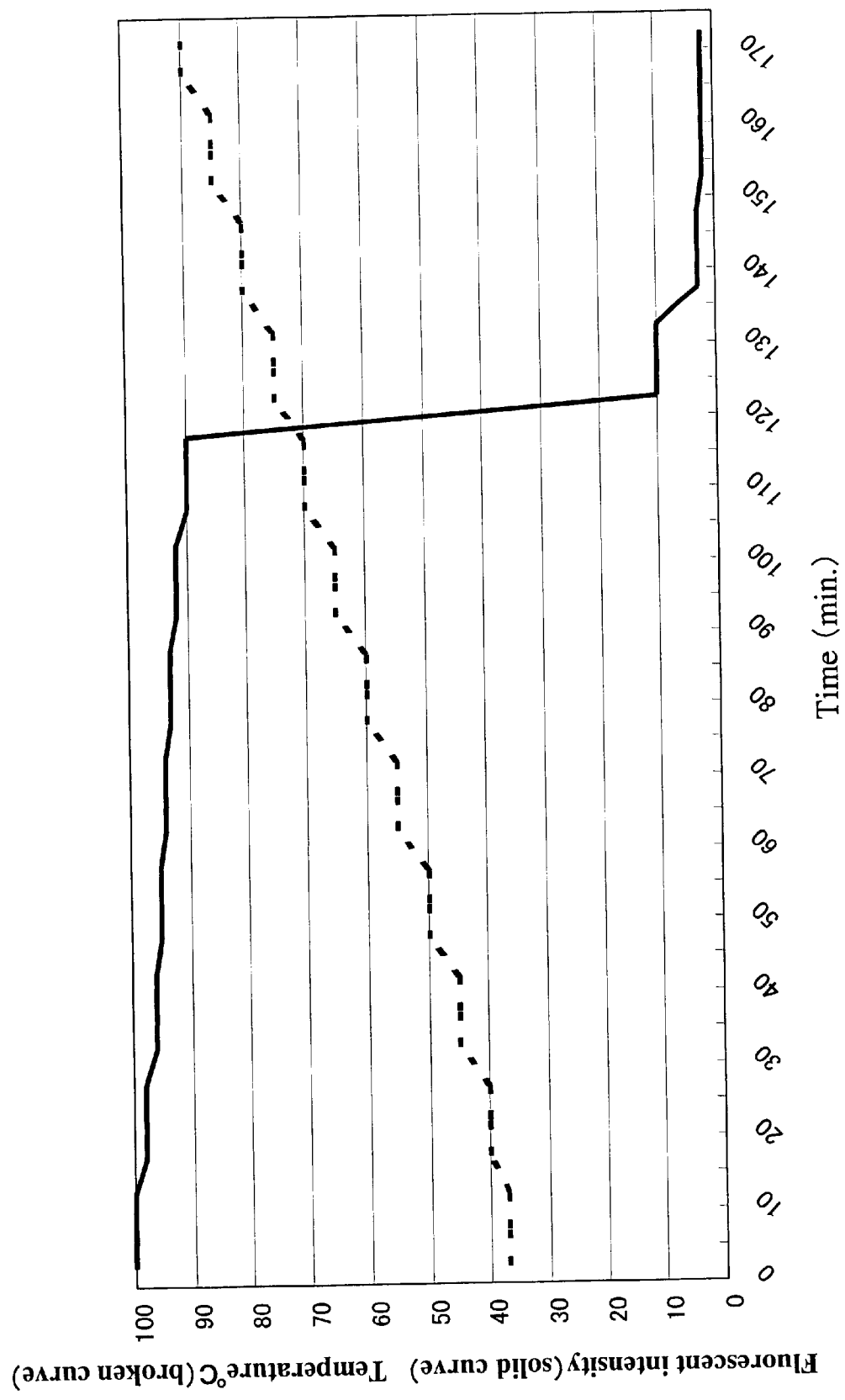
FIG. 11 is a graph representing changes of a fluorescent intensity of a single spot with time as well as changes of a temperature of a biochip.
Figure 13:
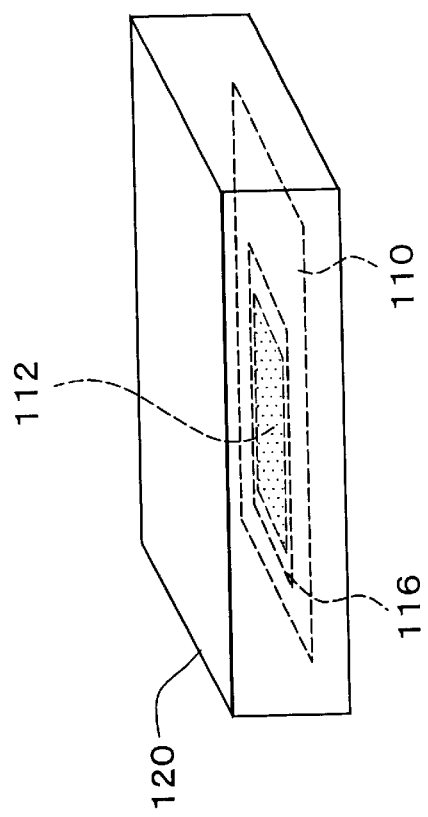
FIGS. 13A and 13B are schematic views illustrating a conventional method.
Figure 13:
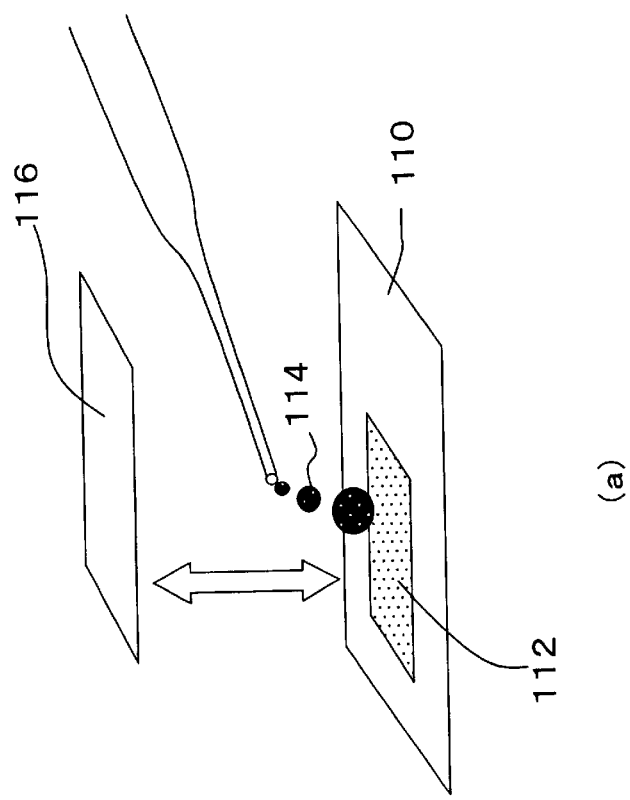

As described above, the fluorescent intensities of individual spots and the background values thereof are calculated for each image, based on which a graph indicating changes of fluorescent intensities with time (changes with temperature) is formed. Once the background region and the sample region are selected by using the region selection tools 81 and 82, the same regions are selected on other images and thus there is no need of selecting these regions for more than once. The regions may be selected automatically based on coordinates data or the like of each FIG. 11 is an exemplary graph formed based on the data accumulated in the computer 40. The graph shows changes of a fluorescent intensity of a single spot on the biochip 10 with time, as well as changes of a biochip temperature. The horizontal axis and the vertical axis represent time and a fluorescent intensity or a temperature, respectively. In the graph, the solid curve represents the fluorescent intensity while the broken curve represents the temperature. The fluorescent intensity is generally the highest at the initiation of hybridization at a low temperature, and thus is indicated as 100%. According to the present example, the temperature of the biochip 10 is stepwisely raised by 5° C. to observe the changes of fluorescent intensity of the sample spot. As the temperature is raised, sample DNA with lower complementation (weaker binding ability) begin to dissociate from the probe DNA. The dissociated sample DNA is removed from the spots with the washing solution. Accordingly, the amount of hybridized fluorescence-labeled sample DNA decreases with lapse of time, and so as the fluorescent intensity. In addition to the fluorescent intensity curve of the spot, a temperature curve is also drawn in FIG. 11. From this temperature curve, the temperature (° C.) when the sample DNA actually dissociated from the probe DNA can be viewed by referring to the temperature at which a rapid fall of fluorescent intensity took place. In FIG. 11, it can be viewed that the sample DNA is dissociated at the first half of 70° C. level. In this case, the dissociation temperature of the sample DNA hybridized to the spot portion of interest is judged to be the first half of 70° C. level. This graph can be displayed and confirmed on the display unit 11 as necessary.

In general, an optimal hybridization temperature (dissociation temperature) can be calculated by following [Equation 1] above based on the number and types of constitutive bases. Accordingly, when the calculated dissociation temperature substantially equals the dissociation temperature judged from FIG. 11, hybridization took place for sure. On the other hand, when the two dissociation temperatures are obviously different from each other, then the binding of the sample DNA is non-specific.

For judgment based on the dissociation temperature estimated by calculation, an effective intensity is calculated (S35). As shown in FIG. 11, when there is a rapid fall in the fluorescent intensity around the estimated dissociation temperature, the fluorescent intensity immediately before the rapid fall can be considered as the fluorescent intensity of the sample DNA of interest. The fluorescent intensity that rapidly fell around the estimated dissociation temperature, indicated as a percentage of the fluorescent intensity upon the hybridization at a low temperature (100%), should be close to 100% when the probe DNA is completely under a specific hybridization. Thus, by indicating the effective intensity in %, it can be used as an index of reliability of the spot on the biochip 10.

As shown in FIG. 12, the estimated dissociation temperature 92 calculated based on the nucleotide sequence of the known probe DNA immobilized on the spot and the effective intensity 93 are displayed in conjunction with a spot ID 91 for the spot on the biochip 10 (S36); and the judgment 94 as to the presence of hybridization is displayed, as a table (S37). In FIG. 12, the results of the judgment are indicated such that ⊙ represents an effective intensity of 80% or higher, ○ represents 65% or higher, Δ represents 40% or higher and X represents less than 40%. By displaying the judgment based on the effective intensity, hybridization at each spot can be detected with high reliability. The effective intensity of each spot or the results of the judgment (⊙, ○, Δ, X) may be adapted to brightness or color to be displayed on a corresponding location on the biochip. Thus, the hybridization status of each spot on the biochip can visually be confirmed.

According to the present invention, hybridization at each spot on the biochip can quantitatively be detected with higher reliability than a conventional method.

What is claimed is:

1. A method for detecting a hybridization reaction, comprising the steps of:

placing, in a container, a biochip having a reaction region on which a plurality of probe biopolymers are separately spotted;

injecting a sample biopolymer into the container;

maintaining the biochip in the container at a constant temperature;

taking images of the reaction region of the biochip at predetermined timings while running a washing solution into the container and while changing the temperature of the biochip according to a predetermined time pattern; and analyzing fluorescent intensities of individual spots based on the images,
wherein the sample biopolymer is fluorescence-labeled.

2. A method for detecting a hybridization reaction according to claim 1, wherein degrees of the hybridization reactions between the sample biopolymer and the individual probe biopolymers immobilized on the spots are detected based on changes of a fluorescent intensity of each spot with time.

3. A method for detecting a hybridization reaction according to either one of claim 1 or 2, further comprising a step of acquiring information of a temperature at at least one of the spots upon a rapid fall of the fluorescent intensity therein.

* * * * *